(12) United States Patent
Hagenbuch et al.

(10) Patent No.: US 9,918,812 B2
(45) Date of Patent: Mar. 20, 2018

(54) TOOTH PRODUCED IN A MOLD, AND DENTAL PROSTHESIS

(71) Applicant: Ivoclar Vivadent AG, Schaan (LI)

(72) Inventors: Konrad Hagenbuch, Haag (CH); Marion Eder, Meran (IT); Martin Bertagnolli, Naturns (IT); Christian Frei, Naturns (IT); Karl Lanbacher, Laas (IT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 14/650,434

(22) PCT Filed: Dec. 6, 2013

(86) PCT No.: PCT/EP2013/075853
§ 371 (c)(1),
(2) Date: Jun. 8, 2015

(87) PCT Pub. No.: WO2014/090706
PCT Pub. Date: Jun. 19, 2014

(65) Prior Publication Data
US 2015/0313693 A1    Nov. 5, 2015

(30) Foreign Application Priority Data
Dec. 12, 2012 (EP) .................... 12196788

(51) Int. Cl.
*A61C 13/08* (2006.01)
*A61C 13/093* (2006.01)
*A61C 5/70* (2017.01)

(52) U.S. Cl.
CPC ........ *A61C 13/081* (2013.01); *A61C 13/1006* (2013.01); *A61C 5/70* (2017.02)

(58) Field of Classification Search
CPC ..... A61C 13/08; A61C 13/081; A61C 13/083; A61C 13/09; A61C 13/1006; A61C 5/08
See application file for complete search history.

(56) References Cited

U.S. PATENT DOCUMENTS

2006/0281051 A1*  12/2006  Koller ................ A61C 13/1006
                                                                       433/198
2010/0028835 A1   2/2010  Hanson et al.
2010/0266988 A1  10/2010  Satoh et al.

FOREIGN PATENT DOCUMENTS

| CH | 336159 A | 2/1959 | |
| DE | 328172 C | 10/1920 | |
| DE | 954368 C | * 12/1956 | ......... A61C 13/1006 |
| DE | 1075794 B | 2/1960 | |
| FR | 657069 A | 5/1929 | |
| FR | 855403 A | 5/1940 | |
| JP | 47916 | 12/1918 | |
| JP | 198999552 | 4/1989 | |
| JP | 2005-066166 A | 3/2005 | |

* cited by examiner

*Primary Examiner* — Julianna N Harvey
(74) *Attorney, Agent, or Firm* — Ann M. Knab; Thad McMurray

(57) ABSTRACT

The invention relates to a tooth made of ceramics, a composite or plastic, which is produced in a mold, said tooth having a basal surface (16) that comprises a trough (18). The especially elliptical or circular trough (18) is adapted to the basal surface (16) and has a trough edge (22, 24) which extends at least partially in an angle of more than 45 degrees, in particular more than 60 degrees or 70 degrees, with respect to the adjacent basal surface (16).

24 Claims, 3 Drawing Sheets

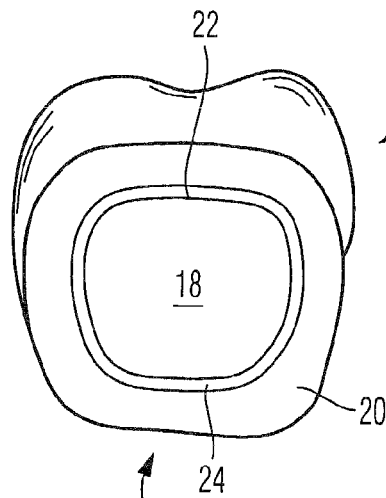
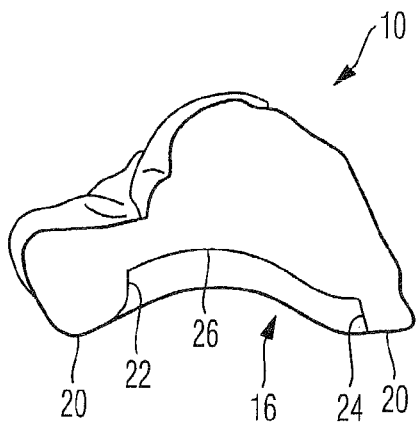
Fig. 3    Fig. 4
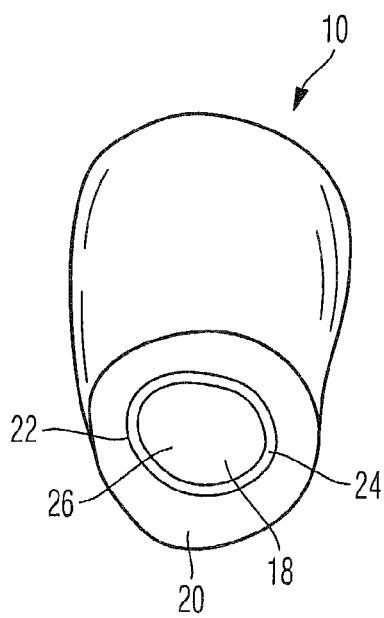
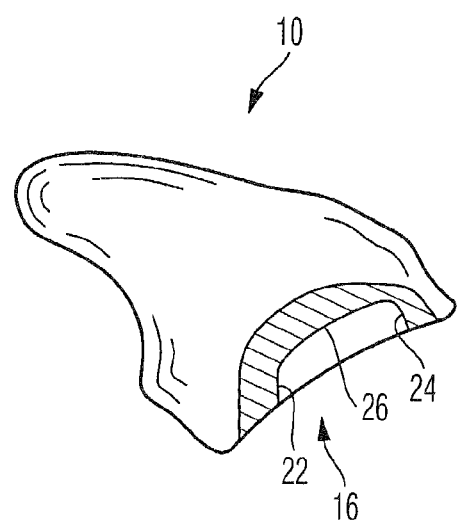
Fig. 5    Fig. 6

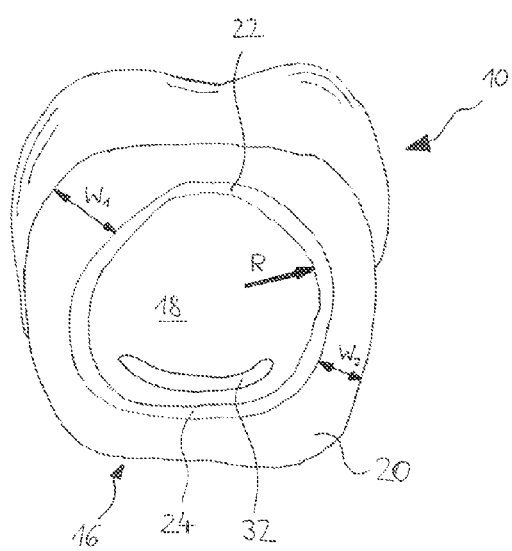
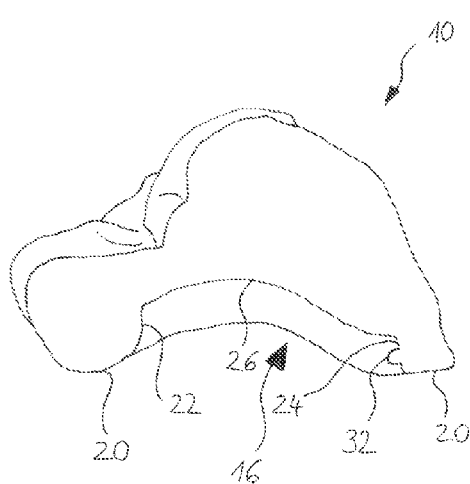
Fig. 7
Fig. 8

TOOTH PRODUCED IN A MOLD, AND DENTAL PROSTHESIS

CROSS-REFERENCE TO RELATED APPLICATIONS

This application is a National Stage application of International patent application PCT/EP2013/075853 filed on Dec. 6, 2013, which claims priority to European patent application No. 12 196 788.9 filed on Dec. 12, 2012, the disclosures of which are incorporated herein by reference in their entirety.

The invention concerns an artificial teeth for use in the manufacture of dentures.

It has been known for a longer time to use artificial teeth as dental replacements, which teeth can be manufactured out of various materials, such as ceramics, but also of plastics or of composite material. Such teeth can be used inside the mouth of a patient as a part of a crown, or via what is referred to as an abutment and an implant. For manufacturing such teeth, molds are usually provided which impart different shapes to the teeth—insofar modeling them on natural teeth—, in order to deliberately imitate a natural appearance. In part, such teeth are also ground and are typically also constructed out of a number of layers in order to give the toot a translucent appearance. Finally, they are also often finished with the help of stains.

Teeth, which together form a set of teeth, were already developed at the turn of the century from the 18$^{th}$ to the 19$^{th}$ century. They are typically attached via their bottom surface which is referred to as basal surface, in most cases with the help of an adhesive, or additionally with the help of a pin, in which case corresponding drillings give mechanical support.

Since about the end of the 1990s, what is referred to as a basal depression has become tried and tested, which slight depression is formed in the basal surface and is suitable for making possible the attachment with the help of a corresponding counter-form, for instance by means of adhesive bonding. In this, it is favorable that a certain re-adjustment is still possible when the adhesive has been applied, i.e. an exact adjustment of the desired angular position and spatial position otherwise.

Such slightly curved basal depressions have been commonly used for a longer time, in which respect reference is to be made, by way of example, to DE 198 29 639 A1 (cf. FIG. 4, reference number 12a) and DE 199 45 354 A1. Another example for such teeth are the Applicant's SR Orthosit teeth.

Teeth need to be produced in numerous different sizes and shapes. In this respect, reference is to be made to the front tooth of a child as compared with a molar of an adult; the differences can insofar amount to more than five times the volume.

This makes necessary a correspondingly intense stock-keeping and a correspondingly high effort in production.

In order to make production more efficient, numerous teeth, such as 28 teeth, are typically manufactured together in corresponding mold depressions of one mold, and are released from the mold in the process of demolding. During demolding, the individual teeth need to be correctly allocated, for which purpose a lot of cost-intense manual work is necessary.

In contrast, the invention is based on the task of manufacturing a tooth in accordance with the preamble of claim 1, as well as a corresponding set of teeth, which has been optimized with regards to handling and also to its workability, without abandoning the favorable optical and strength characteristics of known teeth.

It is particularly favorable, in accordance with the invention, to put into practice a basically bowl-shaped depression, i.e. a depression with a firm depression flank and a depression bottom surface which is extending essentially perpendicular to the former. Such a basal bowl is multi-functional because it makes possible a safe support of the teeth, for instance when they are painted and when casting edges are milled off, but also the safe attachment in one position during demolding of the mold halves of teeth which are cast in multiple arrangement. While such teeth were often deranged when the mold halves were opened due to their attachment to the upper mold half, which made necessary work-intensive sorting by hand, the basal bowl now acts virtually like a sort of downholder inside the mold. Since the teeth remain safely allocated insofar, automated sorting is possible as well.

With the help of the basal bowl in accordance with the invention, a standardization of the support can be put into practice in a surprisingly easy fashion, of course graded in accordance with the sizes of teeth. With the help of the bowl shape, which is special in accordance with the invention, with a non-circular shaped basal bowl, rotation is virtually automatically prevented, and such the retention characteristics of the basal depression can be improved.

Furthermore, it is favorable with teeth manufactured out of three or multiple layers that the basal bowl is shaped in the area of the dentinal material, such that the translucent effect of the enamel material can be maintained completely. In this respect, it is favorable in an advantageous further embodiment if the basal edge surface, i.e. the surface of the basal surface which surrounds the basal bowl, is of essentially consistent width, such that the basal bowl also insofar follows the outer contour of the tooth.

As a result of the "upright" realization of the tooth in injection molding, layers of any layer thickness can be applied in an especially favorable and easy fashion, wherein the layer thickness then corresponds in a basically known fashion to each existing injection-molding cavity for each selected counter form, and wherein the construction of the layers is simply put into practice based on the basal area of the tooth which includes the basal bowl, and wherein the first layer also includes the basal bowl.

It is insofar favorable, in accordance with the invention, if the both basal bowl extends, of consistent depth observed from each adjacent position of the basal edge surface, into the basal surface, and the basal edge surface is of essentially equal width. This will automatically lead to a non-circular realization of the basal bowl, under the precondition that the tooth concerned is not circular.

In an advantageous embodiment, an undercut or a projection in one depression flank is intended, which makes possible an even improved retention. In a further advantageous embodiment, it is intended that the transition between basal surface and depression flank is formed as a hollow groove or fillet.

In an advantageous embodiment, it is intended that the depression (18) is surrounded by a basal edge surface (20) whose minimum width approximately corresponds to the depth of the depression (18) and in particular amounts to approximately 1 mm, or deceeds or exceeds this by 30%.

In an advantageous embodiment, it is intended that the depression (18) takes out a volume from the basal surface (16) which corresponds to at least one twentieth of the volume of the tooth.

In an advantageous embodiment, it is intended that the depression extends transverse to the basal surface (16), essentially perpendicular to the latter, and forms an undercut for a tool support.

In an advantageous embodiment, it is intended that the depression flank extends at least partially at an angle of more than 45 degrees towards the adjacent basal surface, and that the depression is provided with a depression bottom that is formed to be at least partially convex and has a radius of convexity which amounts to at least 50% of the maximum extension of the basal surface.

In an advantageous embodiment, it is intended that the depression is surrounded by a basal edge surface having a varying width, extending around the depression, between approximately 40% of the average width and approximately 200% of the average width.

In an advantageous embodiment, it is intended that the depression is positioned with a depression center essentially in a center of the basal surface and wherein the depression center has a uniform distance to the edge of the basal surface of approximately 0.8 to 1.5 mm.

In an advantageous embodiment, it is intended that a diameter of the depression within one set of teeth is different and is adapted to a size of each respective tooth in the set, such that the width of the basal edge surface remains essentially equal in each tooth of the set.

In an advantageous embodiment, it is intended that the size of the radius of the hollow groove or fillet is one tenth to one third the depth of the depression.

In an advantageous embodiment, it is intended that the varying width, extending around the depression is between 75 and 150% of the average width.

ADVANTAGES OF SUBORDINATE CLAIMS TO FOLLOW

Further advantages, details and features result from the following description of three exemplary embodiments of the invention with reference to the drawings which show:

FIG. 1 a schematic sectional view through a tooth in a first embodiment;

FIG. 2 a partially broken-up perspective view of the tooth in accordance with FIG. 1;

FIG. 3 a bottom view of a molar in accordance with the invention in a second embodiment;

FIG. 4 the molar in accordance with FIG. 3 in a lateral sectional view;

FIG. 5 an incisor in a bottom view as a third embodiment of a tooth in accordance with the invention;

FIG. 6 the incisor in accordance with FIG. 5 in partially broken-up lateral view.

FIG. 7 is a bottom view of a molar in accordance with the invention.

FIG. 8 is the molar in accordance with FIG. 7 in a lateral sectional view.

Figure 1:
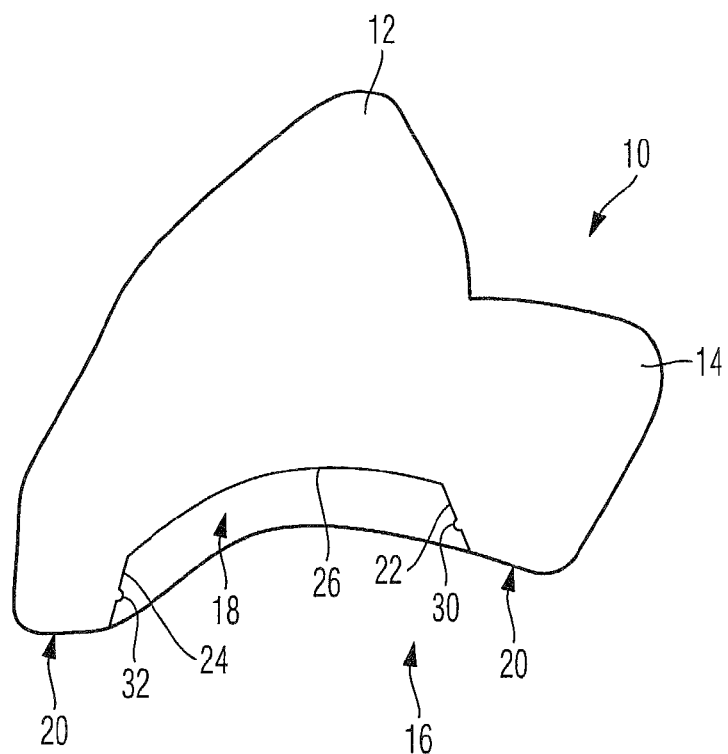

Tooth 10 depicted in FIG. 1 has two humps 12 and 14 in a basically known fashion. On the bottom surface of the tooth, i.e. insofar positioned opposite humps 12 and 14, a basal surface 16 is extending. This is inherently—i.e. also without the invention—centrally recessed and insofar formed to be concave. Into basal surface 16, a basal depression 18 in accordance with the present invention has been cut as a bowl-shaped recess which is particularly shaped.

Laterally of the basal depression extends basal edge surface 20, basically surrounding basal depression 18, and of an essentially consistent width. Adjacent to basal edge surface 20 adjoins a depression flank 22 or 24, respectively.

It extends opposite basal edge surface 20 in the depiction in accordance with FIG. 1 in a left portion, i.e. as a depression flank 24, at an angle of approximately 75° to the basal edge surface, and in the right portion, i.e. as a depression flank 22, at an angle of approximately 50° to basal edge surface 20 there.

Adjacent to depression flanks 22 and 24, depression bottom 26 has been formed. Adjacent to depression flank 22, the depression bottom extends forming a counter-angle there at an angle of approximately 50° to depression flank 22, and adjacent to depression flank 24, depression bottom 26 extends at an angle of approximately 45°. This is because basal edge surface 20 is curved more strongly in the area of depression flank 24, such that due to the recess amount of basal depression 18 and the relocation inwards, i.e. in the direction towards the tooth axis, taking place insofar, the angle between depression flank 24 and depression bottom 26 is smaller there.

Basically, however, it holds true that depression bottom 26 follows basal surface 16 in its extension. Accordingly, basal depression 18 is of essentially consistent depth over its entire extension, and in the drawing, the contour of depression bottom 26 follows basal edge surface 20.

Figure 2:
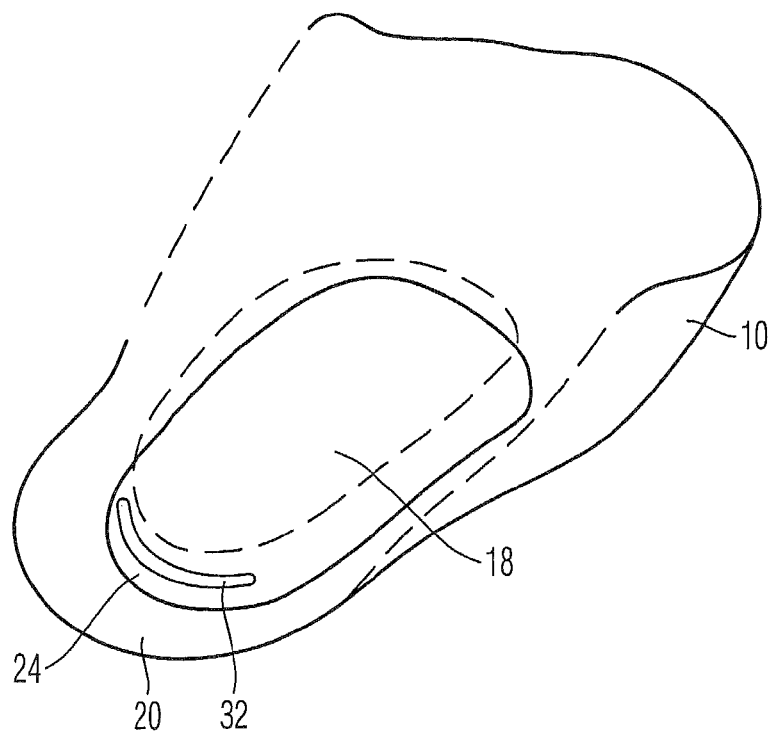

In the embodiment in accordance with FIGS. 1 and 2, an inwardly projecting rib 30 and an inwardly projecting rib 32 are formed at depression flanks 22 and 24, each of which forms an undercut. It is to be understood that instead of this any other shapes are possible that form undercuts. Ribs 30 and 32, respectively, make possible an even further improved attachment of tooth 10.

Basal depression 18 has a shape that clearly differs from the circular shape and also from an elliptical shape. This is well visible from FIG. 2. Rib 32 is depicted there as well, and it is visible that this extends virtually over the entire front surface of basal depression 18.

It is to be understood that the inclination angle of depression flanks 22 and 24 is widely adaptable to the requirements. For example, the inclination angle can be selected to be steeper if an embodiment free of undercuts is desired.

Such a design can be taken from the second embodiment of the invention. FIGS. 3 and 4 show different views of these embodiments. Here as well basal depression 18 is neither circular nor rotationally symmetrical, such that a positionally safe support of tooth 10 is possible. It is well visible from FIG. 3 that basal edge surface 20 is basically of consistent width over its entire extension, with a fluctuation range of +−10%. Basal depression 18 occupies a large portion of basal surface 16, which is, more than 50% of the entire surface. Still the edge, i.e. the basal edge surface and all dental material which surrounds depression flanks 22 and 24, respectively, in the direction towards the outside, is dimensioned such that a safe support is possible.

It can be taken from FIG. 4 that depression flank 22 extends at a steeper angle to basal edge surface 20 than in the embodiment in accordance with FIG. 1. The angle of depression flank 22 to the adjacent basal edge surface 20 amounts to approximately 70°, and the angle of depression flank 24 to basal edge surface 20 amounts to approximately 85°, such that there is an almost perpendicular extension there. Also, with this solution, basal surface 16 is essentially S-curved in its cross section. Accordingly, depression bottom 26 is also S-curved following that extension, and extends here as well in parallel to basal surface 16.

From FIG. 5 an incisor with a basal bowl in accordance with the invention, i.e. a basal depression 16, is visible, which depression extends in a bowl-shaped fashion, i.e. has a flat depression bottom 26, or a depression bottom 26 following basal surface 16 in its extension, and comparatively steep depression flanks 22 and 24 compared with the former.

Basal edge surface 20 is of essentially consistent width over its entire extension, and basal depression 18 is then circularly symmetrical.

From FIG. 6 it is visible that also in this embodiment, comparatively large depression flank angles of depression flanks 22 and 24 have been put into practice, wherein the depression flank angle of depression flank 22 to basal surface 16 amounts to approximately 60°, and that of depression flank 24 to 90°.

Basically, it is also possible to select the basal depression angle at least in one position slightly larger than 90° in order to thus create an undercut.

FIGS. 7 and 8 show a bottom view and lateral sectional view, respectively, of a molar having the same reference numbers as used in drawing FIGS. 1-6.

Here as well depression bottom 26 extends in parallel to basal surface 16, such that a consistent depth of the basal depression in accordance with the invention is provided.

The invention claimed is:

1. A tooth made of ceramics, a composite or plastic comprising
   a basal surface (16) with a depression (18) and a depression flank (22, 24),
   wherein the depression (18) is adaptable to the basal surface (16),
   wherein the tooth can be produced in a mold,
   wherein the depression flank (22, 24) extends at least partially at an angle of more than 45 degrees towards the adjacent basal surface (16), and
   wherein the depression (18) is provided with a depression bottom (26) that is formed to be at least partially convex and has a radius of convexity which amounts to at least 50% of the maximum extension of the basal surface (16), and
   wherein both the depression bottom (26) and the surrounding basal surface (16) are essentially S-curved.

2. A tooth in accordance with claim 1, characterized in that the depression (18) is essentially formed to be bowl-shaped, and the depression bottom (26) is formed to be essentially smooth and extends in a recessed fashion compared with the surrounding basal surface (16) essentially in parallel to the basal surface (16), with depression flanks (22, 24) extending essentially perpendicular towards the depression bottom (26).

3. A tooth in accordance with claim 2, characterized in that the depression (18) is elliptical- or circular-shaped.

4. A tooth in accordance with claim 1, characterized in that one depression flank (22, 24) extends at least partially at an angle of more than 60 degrees towards the adjacent basal surface (16), wherein adjacent to the depression bottom (26) the depression flank (22, 24) extends at least partially at an angle of more than 60 degrees.

5. A tooth in accordance with claim 4, characterized in that at least one depression flank (22, 24) extends almost perpendicular to the basal edge surface.

6. A tooth in accordance with claim 4, wherein the angle at which one depression flank (22, 24) extends is more than 70 degrees towards the adjacent basal surface (16), and wherein the angle at which the depression flank (22, 24) extends adjacent the depression bottom is more than 60 degrees.

7. A tooth in accordance with claim 4, wherein the angle at which one depression flank (22, 24) extends is more than 70 degrees towards the adjacent basal surface (16), and wherein the angle at which the depression flank (22, 24) extends adjacent the depression bottom is more than 70 degrees.

8. A tooth in accordance with claim 1, characterized in that at least one depression flank (22, 24) is provided with at least one undercut, which is formed for providing a pre-determined retentional force, and that the undercut is formed at a pre-determined height at the depression flank (22, 24).

9. A tooth in accordance with ding claim 1, characterized in that a depression bottom (26) is formed as a surface extending three-dimensionally in space without any points of discontinuity.

10. A tooth in accordance with claim 1, characterized in that a transition between basal surface (16) and depression flank (22, 24) is formed as a hollow groove or fillet, with a radius which is distinctly smaller than the depth of the depression (18).

11. A tooth in accordance with claim 10, characterized in that the size of the radius of the hollow groove or fillet is one tenth to one third the depth of the depression (18).

12. A tooth in accordance with claim 1, characterized in that the depression bottom (26) is formed essentially smooth.

13. A tooth in accordance with claim 1, characterized in that heights of the depression flanks (22, 24), observed surrounding the depression (18), are essentially equal and the depression (18) is of an essentially consistent depth.

14. A tooth in accordance with claim 1, characterized in that the depression (18) is surrounded by a basal edge surface (20), the basal edge surface having a width that remains essentially equally wide extending around the depression (18).

15. A tooth in accordance with claim 1, characterized in that the depression (18) is surrounded by a basal edge surface (20) having a varying width, extending around the depression (18), between approximately 40% of the average width and approximately 200% of the average width.

16. A tooth in accordance with claim 15, wherein the varying width, extending around the depression (18) is between 75 and 150% of the average width.

17. A tooth in accordance with claim 1, characterized in that a minimum width of the depression (18) approximately corresponds to its depth.

18. A tooth in accordance with claim 17, wherein the minimum width of the depression (18) is 1 mm, or is within 30% of 1 mm.

19. A tooth in accordance with claim 1, characterized in that the depression (18) is surrounded by a basal edge surface (20) having a width observed in the radial direction of the depression (18) smaller than a radius of the depression, wherein the width, in the case of molars, varies over an extension of a circumference of the depression (18).

20. A tooth in accordance with claim 1, characterized in that the depression is surrounded by a basal edge surface (20) having a width observed in the radial direction of the depression (18) smaller than a radius of the depression, wherein the width, in the case of incisors, does essentially not vary over an extension of a circumference of the depression (18).

21. A tooth in accordance with claim 1, characterized in that the depression (18) takes out a volume from the basal surface (16) which corresponds to at least one twentieth of a volume of the tooth.

22. A tooth in accordance with claim 1, characterized in that the depression (18) is positioned with a depression center essentially in a center of the basal surface (16) and wherein the depression center has a uniform distance to the edge of the basal surface (20) of approximately 0.8 to 1.5 mm.

23. A set of teeth, formed out of teeth in accordance with claim 1, comprising sizes suiting to one another but differing from one another.

24. A set of teeth in accordance with claim 23, characterized in that a diameter of the depression within one set of teeth is different and is adapted to a size of each respective tooth in the set, such that the width of the basal edge surface (20) remains essentially uniform in each tooth of the set.

* * * * *